US009631219B2

(12) United States Patent
Bradley

(10) Patent No.: US 9,631,219 B2
(45) Date of Patent: Apr. 25, 2017

(54) METABOLIC RATE INDICATOR FOR CELLULAR POPULATIONS

(75) Inventor: Michael E. Bradley, Joliet, IL (US)

(73) Assignee: Nalco Company, Naperville, IL (US)

( * ) Notice: Subject to any disclaimer, the term of this patent is extended or adjusted under 35 U.S.C. 154(b) by 170 days.

(21) Appl. No.: 12/711,925

(22) Filed: Feb. 24, 2010

(65) Prior Publication Data

US 2011/0207111 A1    Aug. 25, 2011

(51) Int. Cl.
*C12Q 3/00* (2006.01)
*C12M 1/36* (2006.01)
*C12Q 1/02* (2006.01)
*C12M 1/34* (2006.01)

(52) U.S. Cl.
CPC ............... *C12Q 1/02* (2013.01); *C12M 41/46* (2013.01)

(58) Field of Classification Search
CPC ............ C12Q 1/02; C12Q 3/00; C12M 41/46; C12M 1/36; G01N 33/9406; G01N 2333/924
USPC .................................................. 435/3, 286.1
See application file for complete search history.

(56) References Cited

U.S. PATENT DOCUMENTS

| | | | |
|---|---|---|---|
| 5,043,283 A * | 8/1991 | Endo et al. ............... | 435/296.1 |
| 5,445,946 A | 8/1995 | Roth et al. | |
| 6,117,643 A | 9/2000 | Simpson et al. | |
| 6,369,894 B1 | 4/2002 | Rasimas et al. | |
| 6,555,360 B1 | 4/2003 | Srienc et al. | |
| 6,670,617 B2 | 12/2003 | Banks | |
| 7,024,278 B2 | 4/2006 | Chiappetta et al. | |
| 7,095,500 B2 | 8/2006 | Banks | |
| 7,169,599 B2 | 1/2007 | Barringer, Jr. et al. | |
| 7,198,956 B2 | 4/2007 | Uffenheimer et al. | |
| 7,435,581 B2 * | 10/2008 | West ........................ | 435/289.1 |
| 7,527,924 B2 | 5/2009 | Fleming et al. | |
| 2002/0119438 A1 | 8/2002 | Kato | |
| 2002/0138213 A1 | 9/2002 | Mault | |
| 2004/0043504 A1 | 3/2004 | Buhler et al. | |
| 2004/0157211 A1 | 8/2004 | Skyggebjerg et al. | |
| 2006/0099570 A1 * | 5/2006 | Damgaard et al. ............. | 435/4 |
| 2009/0104652 A1 | 4/2009 | Fleming et al. | |

FOREIGN PATENT DOCUMENTS

| | | | |
|---|---|---|---|
| WO | 0169243 A1 | 9/2001 | |
| WO | 2004015413 A1 | 2/2004 | |

OTHER PUBLICATIONS

McLean et al. A Novel Method for Quantitation of Active Yeast Cells; Technical Report, vol. 2, No. 1-5 (2001) pp. 1-5.*
Siano et al. Nadh and Flavin Fluorescence Responses of Starved Yeast Cultures to Substrate Additions; Biotechnology and Bioengineering, vol. 34 (1989) pp. 660-670.*
Hoppe, H. G. Use of Fluorogenic Model Substrates for Extracellular Enzyme Activity (EEA) Measurement of Bacteria; Handbook of Methods in Aquatic Microbial Ecology(1993), Eds Kemp, P.F., Sherr, B.F., Shaw, E.B., Cole, J.J. (Lewis Publishers, Boca Raton, Fl), pp. 423-431.*
Lomolino et al. Comparison of Esterase Patterns of Three Yeast Strains as Obtained With Different Synthetic Substrates; The Journal of the Instutite of Brewing, vol. 111, No. 2 (2005) pp. 234-236.*
Li et al. Using Molecular Beacons as a Sensitive Fluorescence Assay for Enzymatic Cleavage of Single-Stranded DNA; Nucleic Acids Research, vol. 28, No. 11 (2000) pp. 1-6.*
Peng et al. A Three-Dimensional Flow Control Concept for Single-Cell Experiments on a Microchip. 2. Fluorescein Diacetate Metabolism and Calcium Mobilization in a Single Yeast Cell As Stimulated by Glucose and pH Changes; Analytical Chemistry, vol. 76 (2004) pp. 5282-5292.*
Hottiger et al. Neither Total Culture Fluorescence nor Intracellular Fluorescence are Indicative of NAD(P)H Levels in *Escherichia coli* MG 1655; Applied Microbiology and Biotechnology, vol. 36 (1991), pp. 400-403.*
Jones et al. The Effect of Temperature on the Metabolism of Baker's Yeast Growing on Continuous Culture; Journal of General Microbiology, vol. 60 (1970) pp. 107-116.*
Desouza, G. N. and Kak, A. C., (2002), "Vision for Mobile Robot Navigation: A Survey," IEEE Trans. Pattern Anal. Mach. Intell. 24(2): 237-267.
Orhon et al. Water Sci Technol. 2007;55(10):1-9. "Respirometric assessment of biodegradation characteristics of the scientific pitfalls of wastewaters."

* cited by examiner

*Primary Examiner* — Scott Long
*Assistant Examiner* — Paul Martin
(74) *Attorney, Agent, or Firm* — Leydig, Voit & Mayer, Ltd.

(57) ABSTRACT

Described and claimed is a novel system and method for monitoring the metabolic rate of a cellular population in an industrial process. The invention includes obtaining a sample of the cellular population and initiating a reaction between a metabolic component of the cellular population and a bioreporter. The reaction produces a detectable metabolic signal which is measured and analyzed to determine a metabolic rate of the cellular population. In preferred embodiments, a controller is operable to provide prompts to a user and/or automate various steps of the invention.

12 Claims, 11 Drawing Sheets

2A.

2B.

METABOLIC RATE INDICATOR FOR CELLULAR POPULATIONS

TECHNICAL FIELD

This invention relates generally to a system and method of determining a metabolic rate of cellular populations. More specifically, the invention relates to a system and method of determining the metabolic rate of cellular populations through a signal generated by a bioreporter reaction. The invention has particular relevance to such systems and methods that are manual, semi-automated, or fully-automated.

BACKGROUND

Biological processes appear in many different industrial settings. For example, fermentation processes pervade the biofuels, pharmaceutical, biotechnology, food, and beverage industries. Wastewater treatment is yet another industrial setting where microbiological processes play an important role.

The key performance indicators of industrial bioprocesses, such as final product concentration, process efficiency, and yield, are heavily influenced by the metabolic rates of cellular populations throughout the industrial process (e.g., fermentation and wastewater treatment). In the majority of industrial bioprocesses, however, only environmental parameters, such as temperature and pH, are monitored due to the lack of a simple and rapid way to measure the metabolic activities that are directly responsible for creating the desired product. As a result, most processes are operated without adequate information about the physiological state of biological catalysts used in the process.

Correctly managing cellular populations is generally recognized to be one of the most challenging components of an industrial process or bioprocess. Inconsistent or inaccurate management practices negatively impact the consistency and efficiency of the process. However, the standard method of cellular population analysis by methods such as light microscopy and viability staining presents numerous difficulties and limitations in an industrial production setting. Such difficulties include the inherent variability in results collected by different people due to factors such as the subjective nature of discriminating cells from non-living particles and classifying cells as either alive or dead based on a colored stain applied to the cells. Yet another limitation is that the microscopy method has only two levels for classifying cells: alive or dead. This binary system fails to capture the biological reality that cells exist along a continuous scale from alive to dead and their exact position along this continuum is determined by a multitude of factors.

Numerous examples of methods for quantifying cell concentrations can be found in the prior art. For example, U.S. Pat. Nos. 5,445,946 and 7,527,924 disclose methods and/or devices for cell quandification using fluorescence. U.S. Patent Application Publication 2004/0157211 discloses methods and/or devices for cell quandification using digital microscopy. The major shortcoming of these inventions is that they provide only alternative means of quandifying cellular populations, and not a means of measuring the metabolic rates of cellular populations. To measure metabolic rates, it has historically been necessary to use a method of quandifying the production carbon dioxide and/or consumption of oxygen by cellular populations using instruments such as a respirometer, manometer, or fermontagraph, (See e.g., Water Sci Technol. 2007; 55(10):1-9. "Respirometric assessment of biodegradation characteristics of the scientific pitfalls of wastewaters."). Such instruments, however, are difficult to operate and maintain partially due to the complexities of measuring gasses, which are heavily influenced by temperature, pressure, and interactions with other matter.

There thus exists an ongoing need for improved methods of analyzing cellular populations in industrial settings. In particular, there is a need for methods and systems capable of determining metabolic rates of cellular populations, as opposed to concentration of the cellular populations, while also reducing the inherent variability and difficulties associated with current practices of managing cellular populations in industrial processes.

SUMMARY

The present invention accordingly provides a method for measuring a metabolic rate of a cellular population. In an aspect, the method comprises providing a controller operable to track changes in a parameter. In an embodiment, the parameter is weight and the controller is in communication with a gravimetric device and is operable to track weights of the sample, the bioreporter, and/or the additive and/or changes in weight of matter held within a vessel caused by addition thereof. In another embodiment, the parameter is volume and the controller is in communication with a volumetric device and is operable to track volumes of the sample, the bioreporter, and/or the additive and/or changes in volume of matter within the vessel caused by addition thereof. A signal detector is also in communication with the controller and operable to detect a metabolic signal of the cellular population. The method further utilizes a vessel capable of holding or being associated with at least the following items: (i) a sample of the cellular population or comprising the cellular population, (ii) a bioreporter that is capable of directly or indirectly generating the metabolic signal, and (iii) the signal detector. The sample and the bioreporter are combined in the vessel by adding in any order, including in phases, the sample and the bioreporter to the vessel. One or more additives may also be added to the vessel at any time during implementation of the method. The method also includes optionally tracking changes in the parameter at any time during implementation of the method and optionally recording those changes. The metabolic signal is detected with the signal detector and optionally recorded, as well as the metabolic rate being determined and optionally recorded based upon the detected metabolic signal. Any tracking or recording of the parameter, the metabolic signal, and/or the metabolic rate may take place at one or more times (e.g., at one or more time points). Alternatively, such tracking or recording may take place continuously.

In another aspect, the invention provides a system operable to determine a metabolic rate of a cellular population. The system comprises (i) a controller; (ii) an optional gravimetric device in communication with the controller and/or an optional volumetric device in communication with the controller; (iii) a means of collecting a sample of the cellular population or containing the cellular population; (iv) a bioreporter capable of reacting with a metabolic component of the cellular population in the sample to generate a metabolic signal; (v) a signal detector operable to detect the metabolic signal and in communication with the controller; (vi) a vessel capable of holding or being associated with at least the following items: (a) the sample of the cellular population or comprising the cellular population, (b) the bioreporter, and (c) the signal detector; and (vii) a user interface in communication with the controller.

It is an advantage of the invention to provide an efficient system and method for measuring a metabolic rate of a cellular population in an industrial process.

It is another advantage of the invention to provide a semi-automated or fully-automated system and method for analyzing a metabolic rate of a cellular population in an industrial process.

An additional advantage of the invention is to provide a system and method not subject to sample preparation errors due to entrained gases, particulate matter, or other factors present in the sample that generate imprecise volumetric dilutions.

Another advantage of the invention is to provide sample preparation improvements in the form of an automated and self-correcting method implemented in a user interface that eliminates operator variability in sample preparation practices.

It is a further advantage of the invention to provide a system and method for determining through a chemical reaction with a bioreporter a metabolic rate of a cellular population in an industrial process.

An additional advantage of the invention is to determine metabolic rates of cellular populations in a small amount of time, such as less than ten minutes, and preferably less than three minutes.

Another advantage of the invention is to provide a precise system and method of determining a metabolic rate of a cellular population from an industrial process, where the system and method are robust to varying temperatures, turbidities, and background signals in the measured sample.

A further advantage of the invention is to provide a system and method that is capable of transmitting metabolic rate results in real-time to other information systems within an industrial processing plant, such as databases and control systems, Yet another advantage of the invention is to provide a system and method with adequate precision and a high signal to noise ratio for controlling, diagnosing, adjusting, and/or optimizing industrial processes or bioprocesses based on metabolic rate information.

It is another advantage of the invention to measure metabolic rates with a low level of random error, for example, the measurements should preferably have a coefficient of variation less than 10%, and even more preferably less than 5%.

Yet another advantage is to provide a system and method of measuring metabolic rates that is fast and parallel so as to accommodate the needs of industrial producers with many different concurrent biological processes to manage.

It is yet another advantage of the invention to provide a system and method of detecting the metabolic rate of a cellular population without quantifying the number of cells in the population, either directly or indirectly.

The foregoing has outlined rather broadly the features and technical advantages of the present invention in order that the detailed description of the invention that follows may be better understood. Additional features and advantages of the invention will be described hereinafter that form the subject of the claims of the invention. It should be appreciated by those skilled in the art that the conception and the specific embodiments disclosed may be readily utilized as a basis for modifying or designing other embodiments for carrying out the same purposes of the present invention. It should also be realized by those skilled in the art that such equivalent embodiments do not depart from the spirit and scope of the invention as set forth in the appended claims.

DETAILED DESCRIPTION

Figure 1:
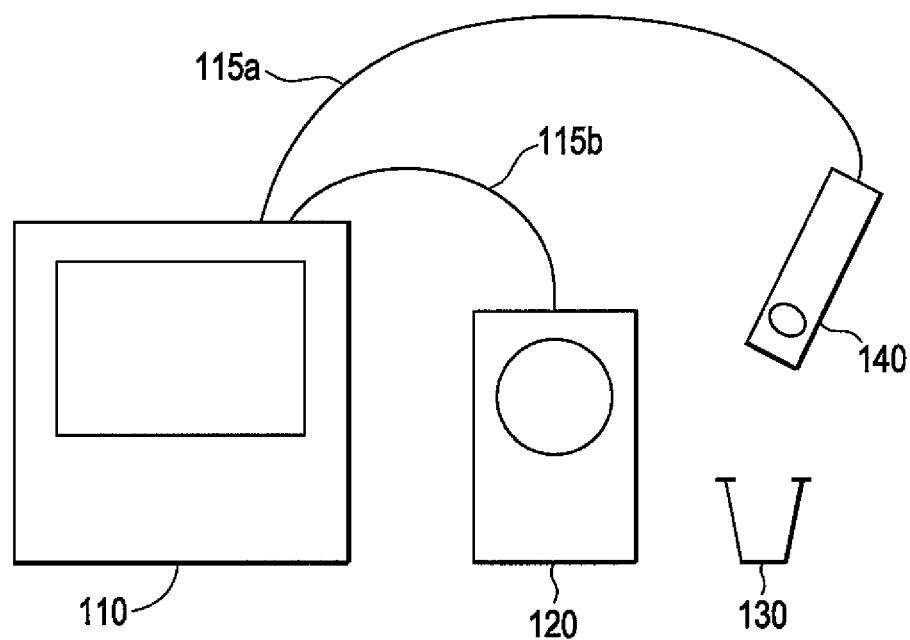
FIG. 1 illustrates an embodiment of the invention including a manual liquid handling station and depicting the various components present in the system of the invention and used in implementing the method of the invention.
Figure 1:
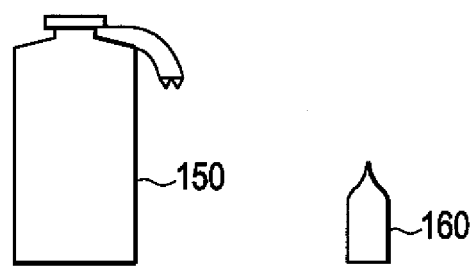

The disclosed and claimed invention is a robust and precise system and method for the detection and monitoring of metabolic rates of cellular populations in industrial processes. As compared to the currently practiced methods, the disclosed system and method improve the state of the art in several ways as detailed herein. The final result of the cumulative improvements is a solution for metabolic rate determinations of a cellular population that is precise and robust regardless of operator technique and sample properties, such as turbidity, temperature, and background signal.

The present invention has application in any industrial setting where cellular populations are encountered. Representative industrial settings having cellular populations amenable to the present invention include production of biofuels, wines, beers, and spirits; preparation of active and inactive yeast intended for use in beverage, fuels, or baking industries; production of nutritional supplements, probiotics, yeast extracts, antibiotics, recombinant proteins, ethanol, or any other industrial yeast product; wastewater treatment systems; algal growth systems; bacterial growth systems; thermal processing systems; cooling water systems; pulp and paper mill activated sludge; other systems; and any combination of the foregoing.

Exemplary cell types include bacteria, archae, protists, microscopic animals, fungi, microscopic plants, animal cells, and any combination of the foregoing. In some embodiments, the invention is also applicable to populations of extremophiles. Nonlimiting examples of certain cell types are given below.

Representative bacteria include (industrial purpose given in parentheses) *xanthamonas campestris* (xanthan gum); *pseudomonas elodea* (gellan (E418)); *lactobacillus delbruekii* var. *bulgaricus* (exopolysaccharides); *lactococcus lacts* var. *cremoris* (exopolysaccharides); *lactobacillus helveticus* (exopolysaccharides); *lactobacillus sake* (exopolysaccharides); *rhodopseudomonas capsulate* (single cell protein); *corynebacterium glutamicum* (L-lysine); *laminaria digitata* (alginate); *ascophyllum nodosum* (alginate); *focus serratus* (alginate); *cyamopsis tetragonolobus* (guar gum); *ceratonia sliqua* (locust bean gum (carob)); *chondrus crispus* (carageenan); *gigartina stellata* (carageenan); *hypea muciformis* (carageenan); *geotrichum candidum* (single cell protein); *zyrnomonas mobilis* (ethanol); *leuconostoc oenos* (malolactic fermentation); *clostridium* (various); *escherichia coli* (various); other bacteria; related species and cell types; the like; and any combinations of the foregoing.

Representative yeast include (industrial purpose given in parentheses) *saccharomyces cerevisiae* (brewing, ethanol, winemaking); *saccharomyces fructuum* (baking); *saccharomyces inusitatus* (baking); *saccharomyces exigus* (baking); *candida crusei* (baking); *candida stellata* (baking); *candida milleri* (baking); *candida utilis* (baking); *torulopsis candida* (baking); *torulaspora delbruekii* (baking); *zygosaccharomyces rouxii* (soy sauce, vinegar); *zygosaccharomyces bailii* (tartaric acid metabolism); *kluyveromyces thermotolerans* (frozen dough); *torulaspora pretoriensis* (brewing); *schizosaccharomyces pombe* (brewing); *schizosaccharomyces malidevorans* (winemaking); *aspergillus oryzae* (sake); *saccharomyces sake* (sake); *saccharomyces kefir* (kefir); *candida kefir* (kefir); other yeasts; related species and cell types; the like; and any combinations of the foregoing.

Representative fungi include (industrial purpose given in parentheses) *aspergillus niger* (enzymes, citric acid, gluconic acid); *sclerotium rolfsii* (single cell protein); *polyporus* (single cell protein); *trichoderma* (single cell protein); *scytalidium acidophilum* (single cell protein); *aureobasidium pullalans* (pullulan); *sclerotium glucanicum* (scleroglucan); other fungi; related species and cell types; the like; and any combinations of the foregoing.

Representative algae include (industrial purpose given in parentheses) *chlorella* (single cell protein); *spirulina* (single cell protein, nutraceuticals); other algae; related species and cell types; the like; and any combinations of the foregoing In a preferred embodiment, the present invention includes a controller operable to receive and process information and provide instructions to a user and/or to various components of the system herein described. The term "controller" refers to an electronic device having components such as a processor, memory device, digital storage medium, cathode ray tube, liquid crystal display, plasma display, touch screen, or other monitor, and/or other components. In an embodiment, the controller includes an interactive interface that guides a user, provides prompts to the user, or provides information to the user regarding any portion of the method of the invention. Such information may include, for example, building of calibration models, data collection, sample placement, bioreporter and additive placement, management of resulting data sets, etc.

The controller is preferably operable for integration and/or communication with one or more application-specific integrated circuits, programs, computer-executable instructions or algorithms, one or more hard-wired devices, wireless devices, and/or one or more mechanical devices such as liquid handlers, hydraulic arms, servos, or other devices. Moreover, the controller is operable to integrate feedback, feed-forward, or predictive loop(s) resulting from the metabolic rate determinations of the invention. Some or all of the controller system functions may be at a central location, such as a network server, for communication over a local area network, wide area network, wireless network, extranet, the Internet, microwave link, infrared link, the like, and any combinations of such links or other suitable links. In addition, other components such as a signal conditioner or system monitor may be included to facilitate signal transmission and signal-processing algorithms.

In one embodiment, the controller is operable to implement the method of the invention in a semi-automated or fully-automated fashion. In another embodiment, the controller is operable to implement the method in a manual or semi-manual fashion. Examples of these variations of the invention are provided below in reference to the figures.

A dataset collected from a cellular population in an industrial process, for instance, may include variables or system parameters such as bioreporter signal, oxidation-reduction potential, pH, levels of certain chemicals or ions (e.g., determined empirically, automatically, fluorescently, electrochemically, colorimetrically, measured directly, calculated, etc.), temperature, turbidity, pressure, process stream flow rate, dissolved or suspended solids, etc. Such system parameters are typically measured with any type of suitable data measuring/sensing/capturing equipment, such as pH sensors, ion analyzers, temperature sensors, thermocouples, pressure sensors, corrosion probes, and/or any other suitable device or method. Devices capable of detecting or sensing colorimetric, refractometric, spectrophotometric, luminometric, and/or fluorometric signals are of particular utility for the present invention. Such data capturing equipment is preferably in communication with the controller and, according to alternative embodiments, may have advanced functions (including any part of the control algorithms described herein) imparted by the controller.

Data transmission of any of the measured parameters or signals to a user, chemical pumps, alarms, or other system components is accomplished using any suitable device, such as a wired or wireless network, cable, digital subscriber line, internet, etc. Any suitable interface standard(s), such as an ethernet interface, wireless interface (e.g., IEEE 802.11a/b/g/n, 802.16, BLUETOOTH™, optical, infrared, other radiofrequency, any other suitable wireless data transmission method, and any combinations of the foregoing), universal serial bus, telephone network, the like, and combinations of such interfaces/connections may be used. As used herein, the term "network" encompasses all of these data transmission methods. Any of the components, devices, sensors, etc. herein described may be connected to one another and/or the controller using the above-described or other suitable interface or connection.

In an embodiment, information (collectively referring to all of the inputs or outputs generated by the method of the invention) is received from the system and archived. In another embodiment, such information is processed according to a timetable or schedule. In a further embodiment, such information is immediately processed in real-time/substantially real-time. Such real-time reception may also include, for example, "streaming data" over a computer network.

Referring now to the figures, it should be appreciated that the characteristics set forth in relation to any of the embodiments depicted in the figures herein may be applied and implemented in relation to any of the other embodiments depicted in the other figures or herein. FIG. 1 illustrates an embodiment of the invention including a manual liquid handling station and depicting the various components present in the system of the invention and used in implementing the method of the invention. In order to obtain precise measurements, the instant invention provides a method of preparing the sample for measurement by combining the sample and required chemical reagents in vessel 130 on weighing device 120 that is in communication with controller 110. Controller 110 is linked to weighing device 120 and signal detector 140 via communication links 115a and 115b. In an embodiment, controller 110 is operable to provide a prompt to a user to place vessel 130 onto weighing device 120. Such a prompt may take the form of a visible and/or audible prompt that the user follows. Such prompts, according to an embodiment, include a certain order of addition into vessel 130. For example, the prompts may suggest target weight values for each component based on previous events. Weighing device 120 then transmits to controller 110 any changes in weight due to the addition of liquids into vessel 130. Controller 110 is further operable to provide a prompt to the user to add a sample of the cellular population taken from an industrial process. The sample may be placed into vessel 130 using any suitable means for transfer. For example, a common method of transferring a liquid sample is through the use of a pipette or other suction-operated device.

The term "vessel" as used in the figures and herein refers to any container capable of holding a volume of liquid and of being weighed on a weighing device. In some embodiments, the vessel further includes a signal detector, a means of controlling the temperature of the liquid held within the vessel, and/or a means of agitating/mixing the liquids held within the vessel. It should be appreciated that any of the vessels or liquid chambers, containers, dispensers, etc. herein described may include a signal detector, a temperature controlling mechanism, and/or an agitation/mixing mechanism.

During the transfer of the sample into vessel 130, weighing device 120 is operable to communicate weight data to controller 110 to track changes in weight of vessel 130 due to such addition of sample. This weight tracking may take place continuously or at one or more time points during the transfer of the sample. Controller 110 is further operable to alert the user to insert signal detector 140 into vessel 130. In another embodiment, signal detector 140 is inserted into vessel 130 prior to or at any time during transfer of the sample into vessel 130. In a further embodiment, signal detector 140 is placed on the outside of vessel 130. In yet another embodiment, signal detector 140 is an integral part of vessel 130. Controller 110 is further operable to provide a prompt, for example visual or audible, to the user to transfer additive 150 (e.g., buffering agent, pH modifying agent, catalyst, coenzyme, mineral, co-substrate, and/or any other additive needed in conjunction with bioreporter 160) and/or bioreporter 160. Weighing device 120 continues to communicate weight change data to controller 110.

At some point during combining the sample with additive 150 and/or bioreporter 160 a reaction takes place that generates a metabolic signal that is detectable by signal detector 140. The metabolic signal may take the form of, for example, a colorimetric, refractometric, spectrophotometric, luminometric, fluorometric signal, or any combinations of the foregoing. To detect the signal, any suitable signal detector 140 may be used The term "signal detector" refers to any suitable device capable of detecting a metabolic activity signal as herein described. In addition, the signal detector may have the capability of detecting more than one type of signal. For example, a particular signal detector may have the capability of detecting more than one wavelength of a colorimetric, refractometric, spectrophotometric, luminometric, and/or fluorometric signal, or may have the capability of detecting a combination of such signals. In another example, the signal detector may be capable of detecting any combination of the foregoing signals and also a turbidity and/or temperature detection and/or measurement. In another embodiment, the term "signal detector" means a combination of a plurality of signal detectors. For example, one signal detector may comprise a flourometer and another may comprise a turbidity meter. It should be appreciated that the term "signal detector" may comprise any combination of the described detectors. Furthermore, the signal detector may be a separate component or may be combined with, for example, the vessel and/or the measuring device as an integrated unit. Though any suitable signal detector(s) may be used, exemplary fluorometric signal detectors are disclosed in U.S. Pat. No. 6,369,894, "Modular Fluorometer"; U.S. Pat. No. 6,670, 617, "Mirror Fluorometer"; and U.S. Pat. No. 7,095,500, "Interchangeable Tip Open Cell Fluorometer."

Figure 2:
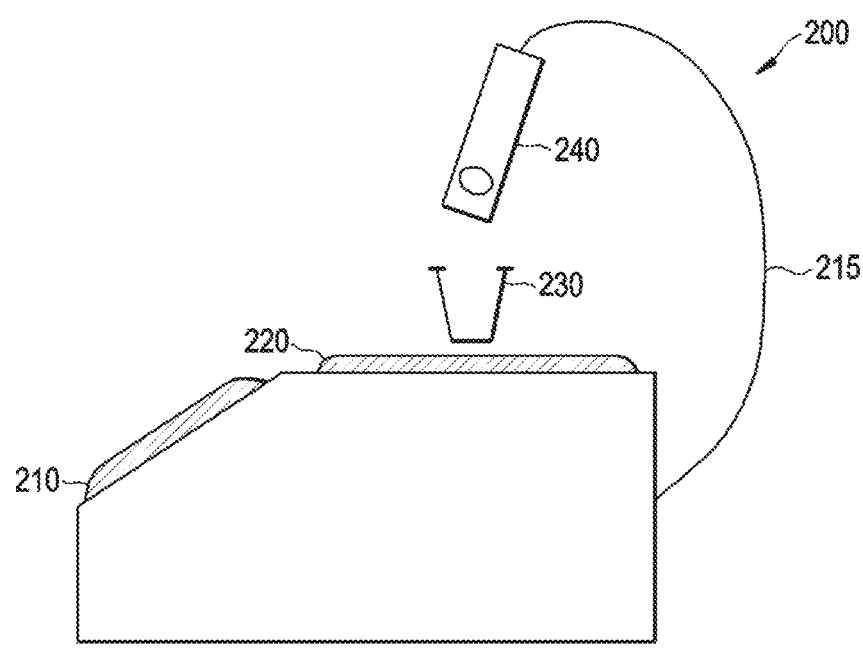
FIG. 2 illustrates an embodiment of the invention including an integrated controller and weighing device with an automated liquid delivery assembly. See FIGS. 2A and 2B.
Figure 2:
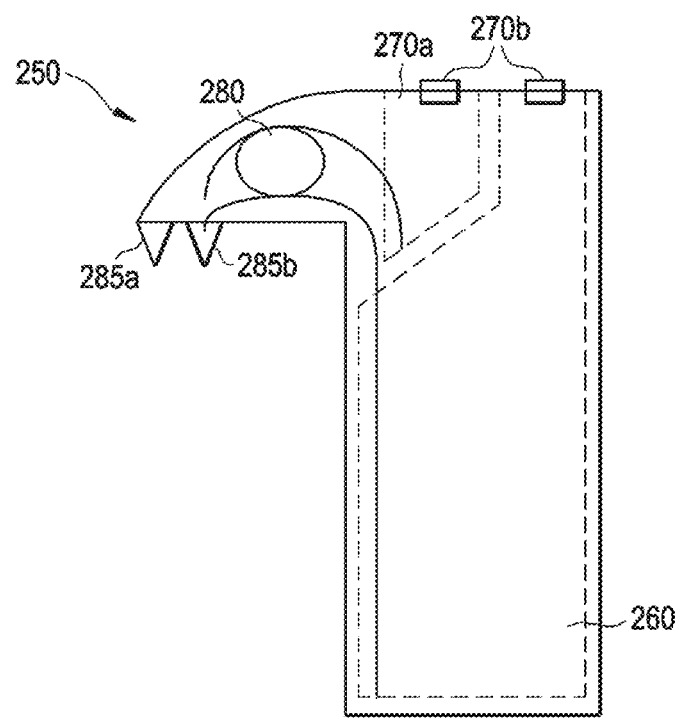

FIG. 2 illustrates an embodiment of the invention including integrated controller and weighing device assembly 200 with automated or semi-automated pump assembly 250. In this embodiment, controller 210 is integrated with weighing device 220 and includes an internal communication link (not shown) for communication between controller 210, weighing device 220, and other components of the system. As described above in relation to FIG. 1 for controller 110, controller 210 is operable to provide prompts or other signals to a user to perform various steps of the method of the invention. As above, controller 210 provides a visual or audible prompt to a user to place vessel 230 onto measuring device 220. Alternatively, a mechanical arm or other device (not shown) may place vessel 230 onto measuring device 220. In another alternative, measuring device 220 and vessel 230 are an integrated unit.

Communication link 215 sends signals from signal detector 240 to controller 210. Signal detector 240 may be introduced into or associated with vessel 230 at any time during addition of the combination of described components into vessel 230. Measuring device 220 then records any changes in weight due to the addition of liquids into vessel 230. Controller 210 is further operable to provide a prompt to the user to add a sample of the cellular population taken from an industrial process. In another embodiment, a mechanical arm or other device aids in adding the sample to vessel 230. Other common methods of transferring a liquid sample, for example, include the use of a pipette or other suction-operated device. During the transfer of the sample into vessel 230, measuring device 220 is operable to communicate weight data to controller 210 to track changes in weight of vessel 230 due to such addition of sample. This weight tracking may take place continuously or at one or more time points during the transfer of the sample. Controller 210 is further operable to alert the user to insert signal detector 240 into vessel 230. In another embodiment, signal detector 240 is inserted into vessel 230 prior to or at any time during transfer of the sample into vessel 230 either manually by the user or automatically through a mechanical arm or other device (not shown). In a further embodiment, signal detector 240 is placed on the outside of vessel 230. In yet another embodiment, signal detector 240 is an integral part of vessel 230.

Controller 210 is further operable to provide a prompt, for example visual or audible, to the user to initiate pump 280 to transfer an additive (e.g., buffering agent, pH modifying agent, catalyst, coenzyme, or any other additive needed in conjunction with the bioreporter) from additive compartment 260 and/or bioreporter compartment 270 for delivery into vessel 230 via dispensing nozzles 285a and 285b. In another embodiment, an automated system comprising a mechanical arm or other device initiates and/or executes delivery of the additive and/or the bioreporter into vessel 230. The sizes of additive compartment 260 and bioreporter compartment 270 may be varied as needed for a particular application. In other embodiments, additional liquid compartments for additional components or backup additive or bioreporter solutions may also be included. Caps 270a and 270b are intended for refilling any needed solutions.

In further embodiments, pump assembly 250 is fully-manual, semi-automated, or fully-automated. Pump assembly 250 is, according to an embodiment, fully-manual where a user initiates the pumping action in response to prompts provided by controller 210. In another embodiment, assembly 250 is semi-automated where a user performs certain functions based on prompts provided by controller 210 and other functions are automated. In a further embodiment, assembly 250 is fully-automated and responds to instructions sent by controller 210 to dispense solutions into vessel 230.

Figure 3:
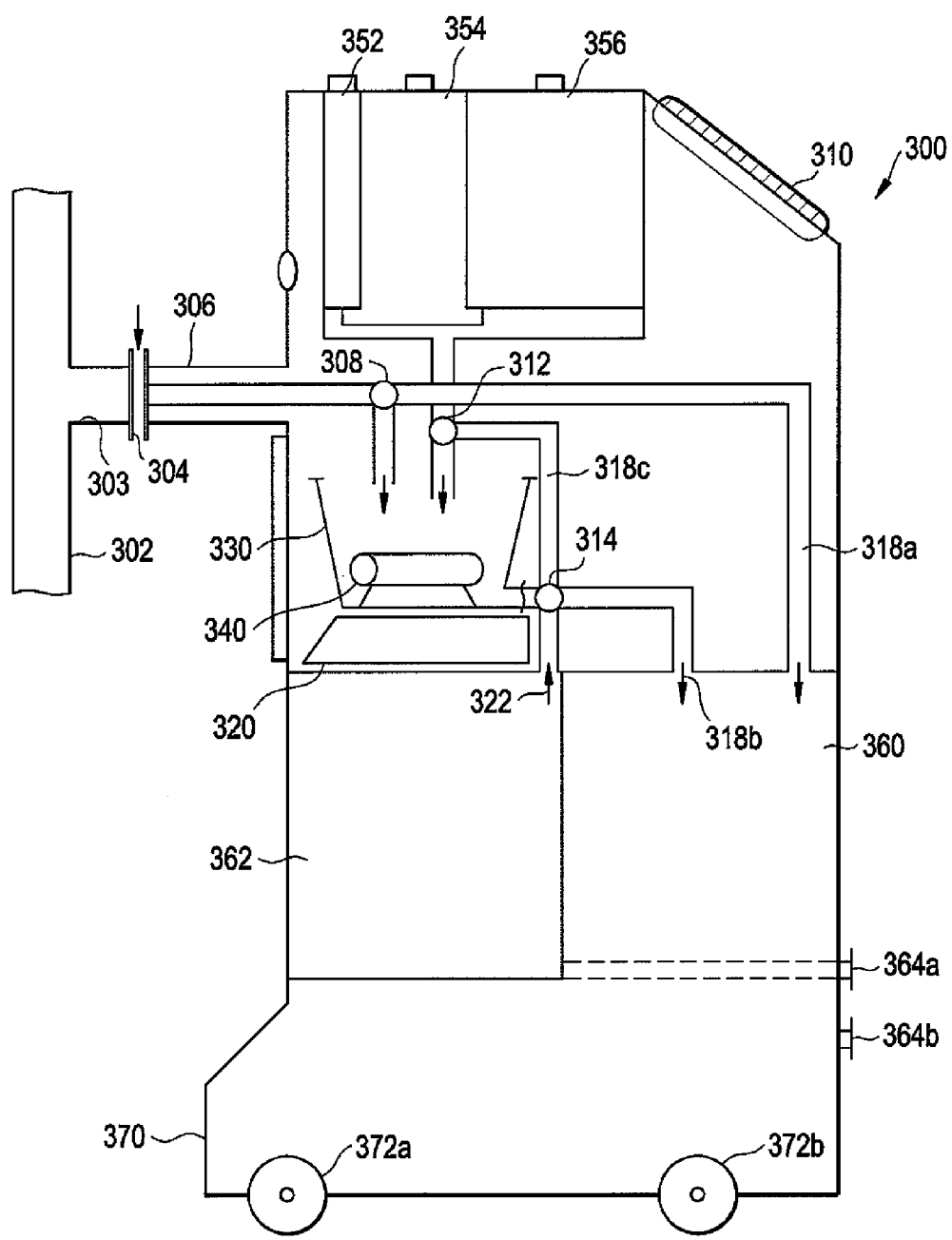
FIG. 3 illustrates an embodiment of the invention including a self-contained unit having automated sample collection, sample handling, liquid delivery, and analyzing features.

In FIG. 3, an embodiment of the invention including a self-contained unit having sample handling and analyzing features is illustrated and shown as mobile unit 300. Any of the functions described below for mobile unit 300 may be fully-automated, or semi-automated. A number of conduits and other channels for flow of samples, bioreporters, solutions, and the like are shown in relation to mobile unit 300. It should be appreciated that additional pumps, valves, or conduits may be included in mobile unit 300 as needed for any particular application. Shown is controller 310 which in communication with several other components of mobile unit 300 and is operable to send instructions to carry out the various described functions. Weighing device 320, vessel 330, and signal detector 340 are shown as an essentially integrated component. It should be appreciated that these components may or may not be permanently attached to each other. In this embodiment, signal detector 340 is shown disposed inside of vessel 330. In other embodiments, signal detector 340 is disposed outside of vessel 330.

Sample collection port 303 may be directly connected or connected via a sample sidestream (not shown) to process tank 302. Process tank 302 may be a main process tank, a secondary process tank, or any suitable access line (e.g., sidestream) to a cellular population in an industrial process. In an embodiment, sample collection port 303 includes a mechanism to create a seal to prevent leaks before, during, and after a connection to sample line 306 is established via joint 304. In an embodiment, joint 304 includes a means to create a fluid communication channel between sample collection port 303 and sample line 306 so as to allow a sample of the cellular population to be drawn into sample line 306. Joint 304 may also include an electronic communication means to allow communication between sample collection port 303 and sample line 306. The electronic communication may be achieved through any suitable means including, for example, conductive pads on the mating surface of the components, one or more electrical connectors, the like, and combinations thereof. When a connection between sample collection port and sample line 306 is made, controller 310 is operable to send instructions to initiate a sample of the cellular population to be drawn and sent to vessel 330 through sample line 306 and valve 308.

In an embodiment, mobile unit 300 includes reagent containers 352, 354, and 356. Although three reagent containers are shown in this embodiment, it should be appreciated that any number of reagent containers may be used. Each of the reagent containers may have its own valve or may have a combined valve that is in fluid communication with more than one of the reagent containers. Such a combination valve is shown as valve 312 in FIG. 3. The reagent containers may house any component of a bioreporter and/or additive as described herein. Conduits 318a and 318b provide a mechanism for exhausted samples, bioreporters, additives, etc. to be discarded. Depending on the particular application, any of the valves shown (e.g., 308, 312, 314) and other valves that may be part of mobile unit 300 actuate to cause spent liquids to travel through conduits 318a and 318b to waste container 360. Other conduits may also be present in mobile unit 300 as needed for a particular application.

In an embodiment, mobile unit 300 further includes wash solution container 362. In FIG. 3, valve 314 is shown as operable to cause wash solution housed in wash solution container 362 to be drawn through conduit 318c. As explained above in relation to the reagent containers, it should be appreciated that any number of wash solution containers may be used. Moreover, each of the wash solution containers may have its own valve or may have a combined valve that is in fluid communication with more than one of the other wash solution containers as needed for a particular application. Ports 364a and 364b are in fluid communication with wash solution container 362 and waster container 360, respectively. The position and number of these ports is exemplary and it should be realized that any number of ports and positioning of ports may be employed as needed for a particular application. Representative wash solutions include water, mild detergent solutions, weak acids, the like, other solutions as needed, and any combinations of such solutions.

In an embodiment, mobile unit 300 may be attached to cart 370 having wheels 372a and 372b. Cart 370 may be, for example, permanently molded into or attached to mobile unit 300 or may be a separate component onto which the remaining components of mobile unit 300 are placed to provide mobility. In an embodiment, mobile unit 300 further comprises a navigation control system (not shown) operable to cause mobile unit 300 to travel automatically or semi-automatically to various locations in an industrial facility and analyze samples of cellular populations therein. Such autonomous mobile robotic devices are disclosed in, for example, U.S. Pat. No. 7,024,278, "Navigational Control System for a Robotic Device" and taught in Guilherme, N. D. and C. K. Avinash (2002), "Vision for Mobile Robot Navigation: A Survey," IEEE Trans. Pattern Anal. Mach. Intell. 24(2): 237-267.

The order of addition of any of the described solutions (e.g., sample of cellular population, bioreporter, additive) may occur in any order as determined by the user and/or the controller as applicable to a particular industrial setting. For example, the sample of the cellular population may be added first followed by the bioreporter and any needed additives, or the bioreporter/additives may be added first followed by the sample of the cellular population. As described herein, changes in weight of the vessel to which these components are added as well as the generated metabolic signal may be tracked and/or recorded in real-time or substantially real-time through communication with the controller.

While the use of a weighing device is the preferred method of sample preparation, other adequate methods of sample preparation that do not require a weighing device are envisioned. In one embodiment, the sample could be prepared volumetrically. For example, the process sample, bioreporter, and any other required additives might manually be added to the vessel by means of a measuring spoon, transfer pipette, medicine dropper, by counting drops, or by pouring. The vessel may also have gradations or zones marked on it to indicate the approximate volume intended for different components. The vessel may be a common laboratory item such as a graduated cylinder, a beaker, or a tube with lines.

In another embodiment, the sample is prepared, either in whole or in part, by the action of mechanical (manual, semi-automated, or fully-automated) pumping. One or several pumps may be employed, and each may be designed to pump at different rates and/or frequencies to accommodate the desired proportions of different components in the final mixture. The pumping action may be controlled by a program that turns the pumps on and off at precisely scheduled intervals in order to achieve precise ratios of the different components. The controller may also receive feedback via level sensors, weight sensors, mass flow meters, volumetric flow meters, other sensors and/or meters, or any combination of the foregoing in order to determine when to switch the pumps on and off. In another embodiment the process sample, bioreporter, and any other additives might be measured by filling void sections of piping or tubing prior to mixing or at the time of mixing. The voids may be filled by a variety of means, for example manually via pouring, by the action of gravity, or by the action of negative or positive pressure. The voids may also be a primed process sample, bioreporter, and any other additives.

The term "bioreporter" refers generally to any molecule capable of reacting with a component inherently present or inducible in the cellular population of the industrial process to generate a detectable metabolic signal. A variety of approaches are available for generating a metabolic signal. The preferred approach is to use a biochemical reporter molecule that reacts with native enzymes to produce a detectable signal. The generated signal should preferably be a light emitting signal, and most preferably be a fluorescent light emitting signal. In alternative embodiments, the generated signal is detectable via methods including colorimetric, refractometric, spectrophotometric, luminometric, fluorometric, or any combinations of the foregoing.

In different embodiments, the bioreporter may take one or more of the following forms: one reagent in one solution; more than one reagent in one solution; more than one reagent each reagent in a separate solution; one reagent in one dry form; more than one reagent in one dry form; more than one reagent each reagent in a separate dry form; the like; and any combination of the foregoing.

In a preferred embodiment, the bioreporter is a molecule or group of molecules that can react with a broad set of enzymes so as to create a detectable signal in a short amount of time. Targeting a broad set of enzymes also ensures that the signal correlates with the overall metabolic rate of the cellular population, and that the approach is feasible for use over a wide range of conditions and metabolic rates. In an embodiment, the set of reaction enzymes is shared almost universally among different organisms. In another embodiment, the set of reaction enzymes is species or cell type specific to allow differentiation among such species, or cell types. In an embodiment, the bioreporter should also be capable of penetrating the cell wall and/or plasma membrane structures to gain access to the cytoplasmic. enzymes. In some cases, this penetration may be aided by the use of other factors, such as detergents. In other embodiments, the sample of the cellular population is subjected to chemical or mechanical shear to lyse the cells and the bioreporter would not need to be capable of such penetration.

In an embodiment, the signal generated by the metabolic activity of the cellular population preferably conforms to certain expected behaviors. For example, the signal should not exhibit an extremely short signal lifetime, and should not suffer from severe dependence on pH, temperature, ionic strength, etc. Effective bioreporters include those substances that are consistently chemically reactive with known components in the cellular population and that do not significantly degrade with time (i.e., have an acceptable shelf life). Preferably the signal intensity should be substantially proportional to its concentration and not significantly quenched or otherwise diminished by other components in the cellular population. Furthermore, the generated signal should be at manageable wavelengths (e.g., other components in the cellular population should not interfere with the signal properties at those wavelengths) and excitation/emission wavelengths (in the case of a fluorescent signal) that are separate from other fluorescent components that may be present.

Representative bioreporters capable of being converted into a molecule that reacts to generate a fluorescent signal for use in the invention include derivatives of naphthalene disulfonic acid; aminomethyl coumarin; pyrene; pyrene tetrasulfonic acid; 4-methyl umbelliferyl; cascade yellow; fluorescein; carboxyfluorescein; BODIPY FL™; BODIPY TR™ tetramethyl rhodamine; rhodamine 110; carboxyrhodamine; lucifer yellow; Hoechst 33342; sulforhodamine 110; resorufin; napthafluorescein; SNARF-1; cyanine dyes; the like; other fluorophores; and any combinations of the foregoing.

To generate a bioreporter molecule, the above-listed or other suitable fluorescent molecules can be, for example, derivatized with a suitable leaving group. The leaving group functions as the enzmatically labile portion of the bioreporter molecule. The leaving group also functions to alter the fluorescent properties of the fluorescent molecule so that the bioreporter is in one fluorescent state when complexed with the leaving group, and in a second fluorescent state when the leaving group is enzymatically cleaved from the core fluorescent molecule.

In another embodiment, a suitable bioreporter configuration involves separating a fluorescent molecule and a quencher molecule by a short biopolymer of nucleic acids, proteins, carbohydrates, or lipids. Many cellular enzymes function to degrade biopolymers. In an embodiment, the bioreporter is a hairpin shaped DNA molecule with an internally quenched flourophore, the fluorescence of which is restored upon degradation of the DNA molecule by nuclease enzymes present in the cellular population. Another suitable bioreporter molecule involves labeling a biopolymer at a high density with one fluorescent molecule that is able to quench its own fluorescence at high local concentrations. Upon degradation of the biopolymer, short segments would be released that fluoresce.

It should be appreciated that the set of possible combinations between leaving groups and fluorescent core molecules, and between biopolymers and fluorophore/quencher pairs, is extremely large and suitable combinations may be determined by one skilled in the art. Nonlimiting examples of certain bioreporter chemistries that are useful within the context of the instant invention are given below.

Representative bioreporter chemistries include (broad classes of target enzymes given in parentheses) 4-methylumbelliferyl glucopyranoside (glycosidase), 6,8-difluoro-4-methylumbelliferyl xylanoside (glycosidase), 6,8-difluoro-4-methylumbelliferyl glucopyranoside (glycosidase), 4-(Trifluoromethyl)umbelliferyl galactopyranoside (glycosidase), fluorescein-di-B-D-glucopyranoside (glycosidase), fluorescein-di-B-D-galactopyranoside (glycosidase), naphthalimide phosphate (phosphatase), 4-nitrophenyl phosphate (phosphatase), 4-methylumbelliferyl phosphate (phosphatase), 6,8-difluoro-4-methylumbelliferyl phosphate (phosphatase), di-O-phosphatidylfluorescein (phosphatase), O-phosphatidylfluorescein (phosphatase), di-O-acetyl 5-chloromethylfluorescein (lipase/esterase), di-O-acetylsulfofluorescein (lipase/esterase), di-O-acetyl 5-(6)carboxynaphthofluorescein (lipase/esterase), 6,8-difluoro-4-methylumbelliferyl butyrate (lipase/esterase), methylumbelliferyl-butyrate (lipase/esterase), 4-(Trifluoromethyl)umbelliferyl butyrate (lipase/esterase), di-O-propionylfluorescein (lipase/esterase), O-propionylfluorescein (lipase/esterase), di-O-butyrylfluorescein (lipase/esterase), O-butyrylfluorescein (lipase/esterase), di-O-acetylfluorescein (lipase/esterase), O-acetylfluorescein (lipase/esterase), resorufin acetate (lipase/esterase), resorufin isobutyloxycarbonyloxy (lipase/esterase), 4-methylumbelliferyl sulfate (sulfatase), 6,8-difluoro-4-methylumbelliferyl sulfate (sulfatase), aminomethylcoumarin-L-leucine (protease), Gly-Pro-aminomethylcoumarin (protease), resazurin (oxidoreductase), fluorophore-polypeptide-quencher (protease), fluorophore-carbohydrate-quencher (glycosidase), fluorophore-lipid-quencher (lipase), fluorophore-polynucleotide-quencher (nuclease); other bioreporters; the like; and any combinations of the foregoing.

An exemplary embodiment of the invention is the following. In the process of preparing the sample for measurement, the instant the bioreporter comes in contact with the cellular population a biochemical reaction begins that produces a metabolic activity signal. The instant invention employs several methods to eliminate variability in metabolic rate measurements due to reaction timing. First, the controller/weighing device pairing automatically records the precise moment that the bioreporter solution contacts the cellular population sample. This was a shortcoming of the prior art since the user was responsible for both mixing the solutions and starting the timer. Second, the reaction start time recorded by the controller/weighing device pairing is used by the controller/signal detector pairing to automatically measure the signal in the prepared sample at precisely timed intervals according the instructions operated by the controller. By removing the burden of timing from the human user and automating the responsibility through controller/weighing device and controller/signal detection parings, the invention effectively enables metabolic rate measurements through precise reaction timing.

Another notable advantage of the present invention's signal detector-into-sample embodiment is that progress of the reaction can be monitored continuously from beginning to end, which would be difficult to impossible in the prior art due to the need to transfer the sample between a temperature control device and the detection instrument. With a continuous reaction monitoring system, it is possible to calculate the reaction rate as opposed to the reaction endpoint as practiced in the prior art. Measuring reaction rates is more reproducible than measuring reaction endpoints because the rate calculation takes into consideration the variable background signals present at the beginning of the reaction, the dilutions performed during sample preparation, and the reaction temperatures.

Furthermore, certain signals, especially those detected through optical means, are difficult or impossible to accurately measure in samples with turbidity, or light scattering properties, unless the signal detection instrument has an associated calibration model the captures the effects of sample turbidity on signal strength. The instant invention may employ, for example, a dual channel signal detector, where one channel is designed to measure fluorescence and the other channel designed for measuring turbidity. In addition, the instant invention may utilize a software procedure for building and storing calibration curves that model the signal detector's response to increasing turbidity from the process sample. Together, these improvements allow for accurate signal detection in sample compositions of different turbidities.

In many instances, the described system and method will require calibration to ensure continued precision. Though any suitable method of calibration may be used, it should be realized that calibration of the signal detection instruments in particular is important for several reasons. First, the instruments may drift over time due to internal fluctuations in the signal detection mechanisms. Second, when a plurality of instruments is simultaneously or sequentially used, normalization of inherent differences in signal detection properties aids to produce consistent results. Third, the properties of the samples being measured can change over time. For example, with regard to fluorescence detection, many conventional systems use a quick two-point method of calibration. This method involves calibrating by measuring a blank sample containing no fluorescent signal, and then measuring a second sample containing a standard amount of fluorescent signal. While this approach can work effectively for quantifying fluorescence in samples that contain zero turbidity, the majority of samples of cellular populations encountered in industrial systems possess varying amounts of turbidity. Turbidity effects the detection of fluorescent signals in unpredictable ways. For instance, turbid matter can scatter fluorescent light away from, or towards, the signal detector. Also, turbid matter can absorb excitation and/or emission light and prevent it from exciting the fluorogenic molecules or from reaching the signal detector. For these reasons, it is preferred to calibrate against a mixture of the process sample and a standard solution rather than calibrating against a standard solution.

An exemplary approach to perform such calibration is to build a first calibration curve using a solution with zero fluorescence, and a second curve using a solution with a known amount of fluorescence. Each of the curves should contain three or more measurements made on different proportions of process sample mixed with the respective solutions. Even more preferable is to use a structured calibration work flow encoded in a user interface and to prepare the calibration samples on a digital balance (i.e., weight measuring device) in communication with a controller. In this way, it is possible to build and store multiple models for samples of different compositions, to perform quality control checks as the models are being constructed, and to capture other information such as the total suspended solids (TSS) information for the calibration sample and to use this information to report back the TSS of an unknown sample measured at some point in the future. Yet another advantage to the preferred approach is that it creates a defined calibration space with respect to fluorescence and turbidity, which is useful because samples intended for metabolic rate measurement can be prepared with some flexibility on the digital balance and still fall within the space of the calibration model.

It is well known that the metabolic rate of cellular populations is temperature dependent. Higher temperatures will generally produce higher metabolic rates, unless the temperature becomes too high for the enzymes to properly function. Conversely, lower temperatures typically result in reduced metabolic rates. If the temperature becomes too low, however, the metabolic rate may be reduced to cause the amount of metabolic signal produced via reaction with the bioreporter to be decreased to a level too low to be accurately detected by the signal detector. Several other factors become important under these circumstances (e.g., background signal) and it is generally preferable to avoid measuring rates when the metabolic signal is insufficient. In instances where the temperature range encountered has such an effect, it is preferable to control the temperature of the prepared sample within temperature limits. While this approach offers the possibility of exquisite control, it typically requires specialized equipment and attentive care from the operator to ensure that the equipment is functioning correctly. For example, an effective temperature control scheme might involve the use of temperature controlled reagents, or a temperature controlled environmental chamber in which the measurements are performed, or a vessel equipped with one or more heating elements. If the ambient climate is cold enough, or if the cellular population is small enough, it may be necessary to artificially elevate the temperature of the prepared sample through any necessary means of temperature control to generate a sufficiently high signal for accurate detection and rate calculations.

The preferred approach is to allow the temperature to fluctuate within the limits of room temperature. With this approach it is important to measure the temperature of each reaction, and to have a reasonable correction factor for the metabolic rate of the cells in the prepared sample to correct for fluctuations in temperature. This information would then be used by a software program or other algorithm in the controller to calculate all metabolic rates as if they were collected at a standard temperature. When taking this approach, the temperature normalization algorithm will become increasingly important when the measured temperature is farther from the reporting temperature. For this reason, the standard temperature for reporting metabolic rates might be 24° C. (75° F.) because this is close to the average room temperature. However, the reporting temperature can be set to other values if desired.

Previous attempts to manage the influence of temperature on biological reactions involved the use of various strategies to control the reaction temperature. These methods were problematic because the temperature control was difficult to manage, the temperature difference between the desired and actual temperature was usually unknown, and because the user was responsible for transferring the sample between a temperature control device and the signal detection instrument. To overcome these limitations and eliminate the measurement variability that they inherently introduce, the invention advances the state of the art on several fronts. First, the invention, for example, may utilize a signal detector-into-sample approach as opposed to a sample-into-cuvette-into-signal detector approach found in the prior art.

The invention may also utilize a signal detector with a built-in thermistor, or digital thermometer. The signal detector-into-sample approach and the built in thermometer enable direct measurement of the sample temperature during the reaction because the signal detector is not separated from the sample by a plastic or glass cuvette. The improved method may also utilize the reaction temperature data and a temperature correction algorithm to report the metabolic rate at a standardized temperature each time. As a result, the user is free from the burden of using a temperature control device or even from knowing the temperature of the reaction.

In some cellular populations, substances that interfere with accurate metabolic signal measurements may be present, or when the cellular population is a mixed population of more than species. In such cases, it may be desirable to apply filtration or other means of separation (e.g., centrifugation, coagulation, or floatation) before or after the metabolic rate measurement. Separation of interference-causing substances or separation by species and/or cell size may be desirable to produce more specific and valuable measurements of metabolic rate. For example, in a mixed population a certain species may produce an enzyme that predictably reacts with the bioreporter to produce a precise signal for determining metabolic rate and another species may produce an enzyme that quenches the signal or inhibits the reaction. Moreover, it may desirable to collect a sample of the cellular population, separate one or more cell types or species (or simply separate all cells) from the medium present in the industrial process, and re-suspend the cells in another solution (e.g., buffer or water) to enhance the reaction with the bioreporter. In other cases, it may beneficial to dilute the obtained sample. In these embodiments, the controller would be further operable to correct any measurements according to a dilution factor correction.

Another significant improvement of the present invention over the prior art relates to the benefits of using a computer software program to conduct various elements of the method. At a basic level, the software provides the benefit of improved accuracy and reduced errors attributable to assigning tasks to the computer that were previously assigned to the human operator. For example, by not having to manually transfer metabolic rate information from the instrument to a permanent storage location, such as record book, spreadsheet, or database, the integrity of the information is conserved. The software program ensures the reliability of the system by guiding the measurement process all the way from sample preparation, data collection, numerical calculations, and results archiving. Such a system can be useful for improving process operations by enabling the comparison of operators, conditions, and even performance across plants within the same company. At a higher level, the software program enhances the functionality of the system by enabling features that would be difficult to impossible using methods known from the prior art. For example, each measurement may collect >100 data points and perform >50 calculations before deriving the final metabolic rate for that sample. In addition, the digital information resulting from the use of software driven measurement systems allows for further value to be derived from the measurement. For example, it is now possible to input metabolic rate data to a model-based control algorithm intended to monitor and improve the state of the process. Likewise, data collected with the system can be viewed in real-time by all interested parties using intranet, extranet, or internet connectivity.

Using any of the embodiments herein described, or any combinations of various elements within those embodiments, the detected metabolic signal is analyzed by the controller. The controller is operable to execute an algorithm, program, executable digital instruction, or the like to determine the metabolic rate of the cellular population based upon the metabolic signal. The metabolic rate is used to implement methods to control and/or manage the cellular population (or any one or more species within the cellular population) for any purpose that is the objective of the particular industrial process being tested.

An example of the basic steps implemented by a controller for processing a metabolic signal to produce a metabolic rate indicator can be understood from the following outline of events. The method includes a first step of converting the arbitrary units of the measured signal into units of defined signal concentration. This conversion is conducted by reference to the calibration model, which defines the amount of signal expected from the signal detector when measuring solutions with known concentrations of signal mixed with varying proportions of process sample at a known temperature. The result of this first step is an accurate measurement of signal concentration that accounts for the interference of turbidity and temperature on signal strength. Converting the measured signal units into units of defined signal concentration occurs at least twice during the measurement procedure, although there is no limit to the number of times that these measurements and subsequent conversions can be conducted.

The second step of processing metabolic signals to produce a metabolic rate indicator involves calculating the magnitude in signal concentration change between the initial measurement time and the final measurement time. The change in signal concentration is divided by the change in time between the initial and final measurement to achieve an average rate of signal change. However, in order to produce a metabolic rate indicator it may be necessary to further process the data to adjust for the influence of sample dilution and sample temperature. Accordingly, the third step may be to multiply the rate of change calculated for the prepared sample by the magnitude of dilution used to prepare the sample. The magnitude of dilution may be determined according to the information transmitted from the weighing device to the controller during sample preparation. The fourth and final step may be to adjust the metabolic rate to account for the difference between the actual temperature at which the reaction was performed and the standard temperature used for reporting. In practice, this may involve converting the metabolic rate measured at the actual reaction temperature into the metabolic rate that would have been observed had the reaction been performed at a different temperature. The metabolic rate at a particular temperature can be calculated using a suitable mathematical equation (e.g., a two-point form of the Arrhenius equation) and a reasonable correction factor if it is known for some other temperature.

The foregoing may be better understood by reference to the following examples, which are intended for illustrative purposes and are not intended to limit the scope of the invention.

Example 1

Metabolic Rate of Carbon Dioxide Formation

Figure 4:
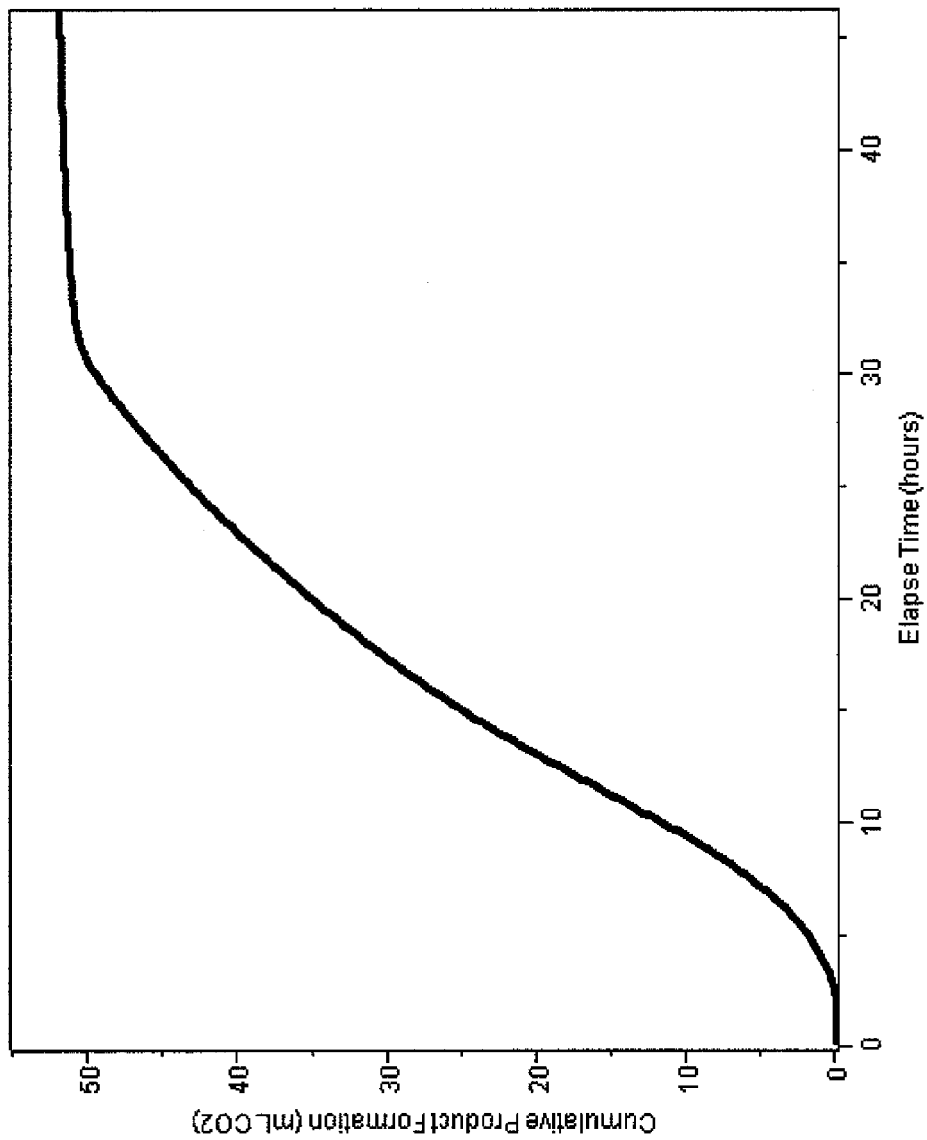
FIG. 4 illustrates fermentation performance that was monitored by tracking cumulative product (carbon dioxide) formation over time where the rate of product formation at any point during batch fermentation can be obtained by the slope of the cumulative product curve.
Figure 5:
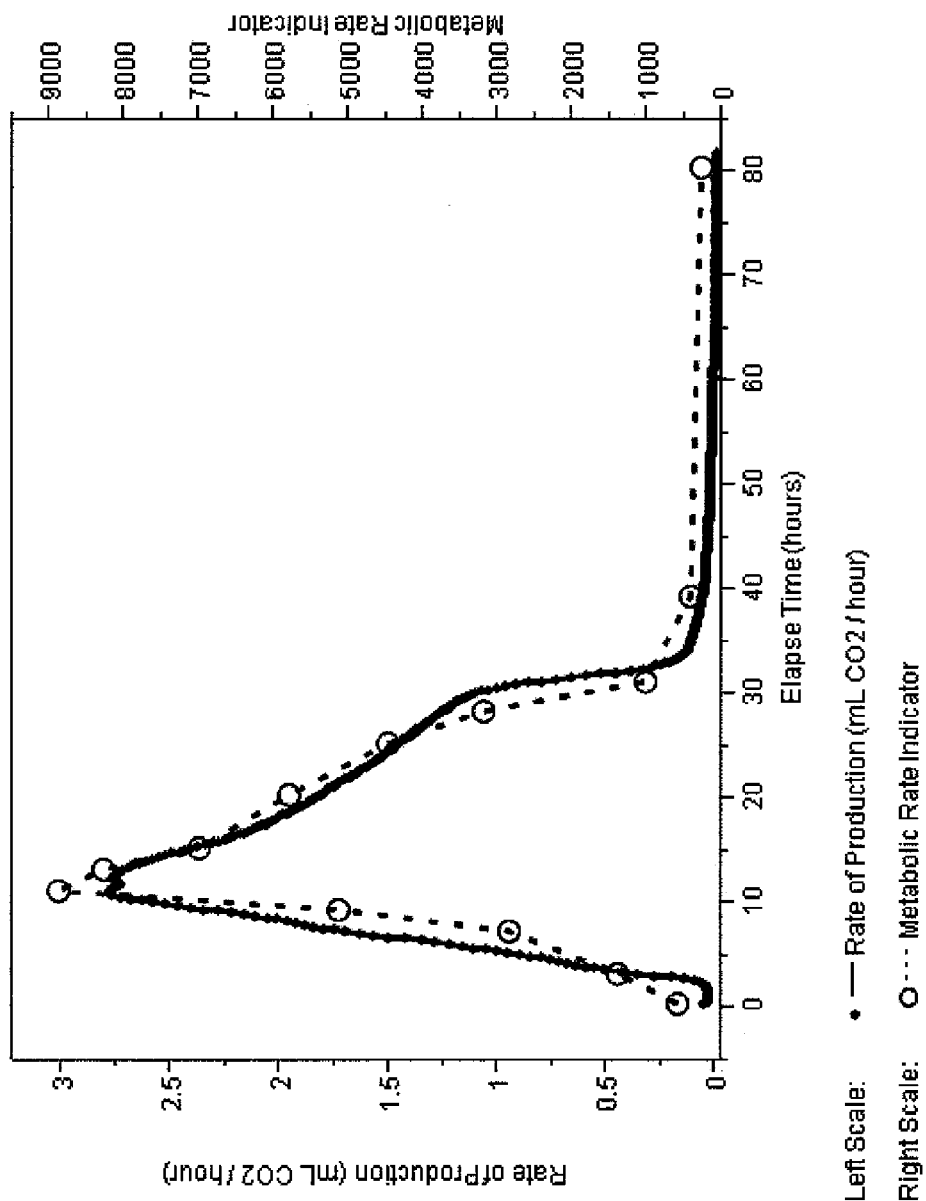
FIG. 5 illustrates an embodiment of the invention where the metabolic rate indicator and the rate of carbon dioxide production are strongly correlated.

In this example, it is demonstrated that the metabolic rate indicator of the instant invention correlates with the actual rate of product (carbon dioxide) formation during batch fermentation. A batch fermentation of liquefied corn mash (32% total solids) was performed with newly propagated yeast. Fermentation performance was monitored by tracking cumulative product formation over time with a continuous carbon dioxide off-gas analyzer (FIG. 4). The rate of product formation at any point during batch fermentation can be obtained by the slope of the cumulative product curve. As shown in FIG. 5, the rate of product formation and the metabolic rate indicator of the instant invention will show a strong correlation using the bioreporter di-O-propionylfluorescein and a pH 7.6 buffer will show a strong correlation.

Example 2

Independent Signal Detectors, Operators, and Batch Fermentations

Figure 6:
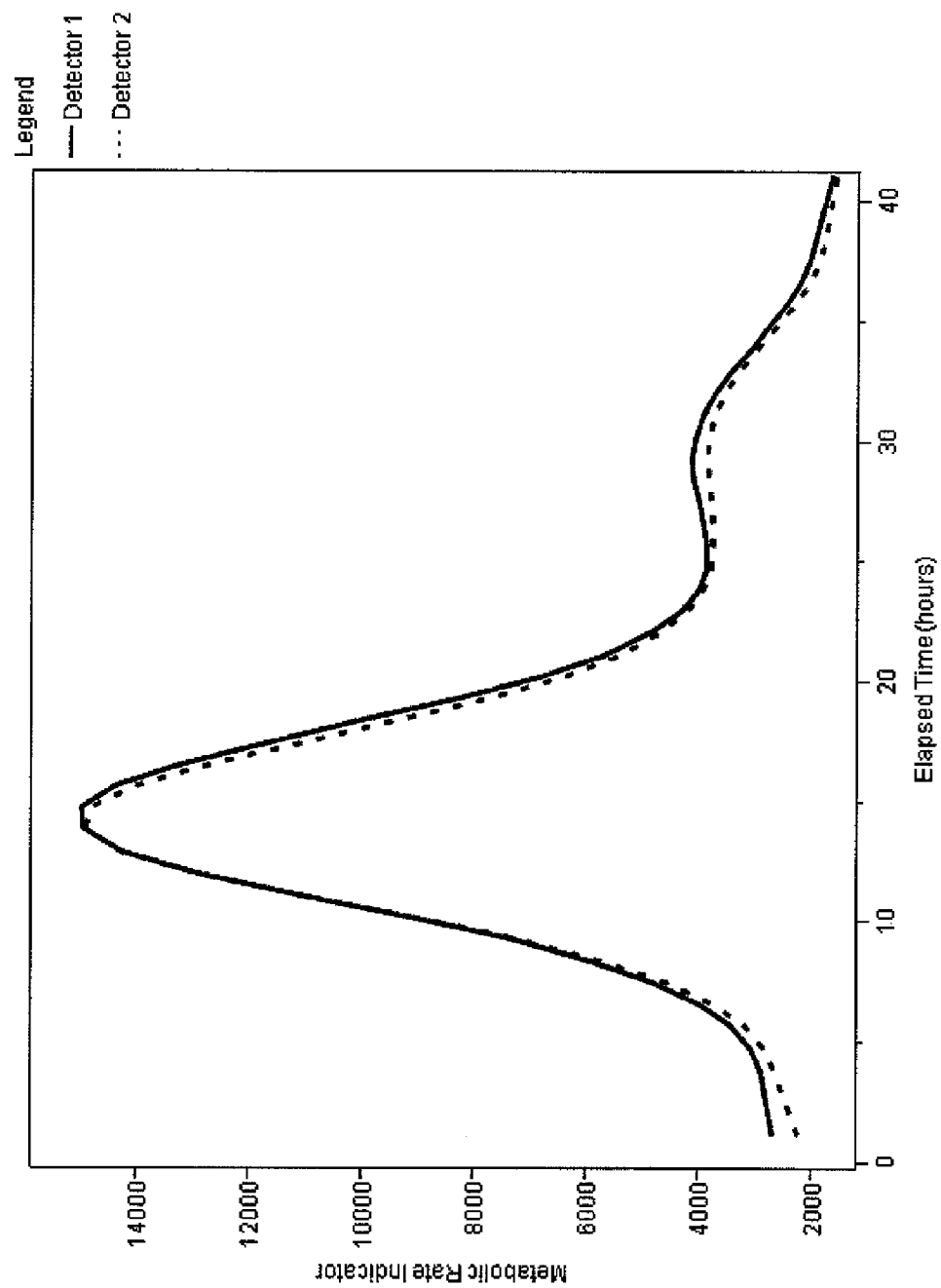
FIG. 6 illustrates an embodiment of the invention that effectively produced consistent results across different operators, signal detectors, and batch fermentation processes.

This example illustrates the consistent performance of the metabolic rate indicator across different operators, signal detectors, and batch fermentations. Over a one month period, five different operators collected a total of 300 metabolic rate measurements with the system of the invention using the bioreporter di-O-acetylfluorescein and a pH 7.6 buffer across 25 different batch fermentations in an industrial ethanol plant. Each sample was tested once with a first signal detector unit and then re-tested with a second signal detector unit. The signal detectors were periodically calibrated against a mixture of the process sample and standard solutions during the one month trial. As shown in FIG. 6, the method produced consistent results across different operators, signal detectors, and batches.

Example 3

Metabolic Rate of Ethanol Formation

Figure 7:
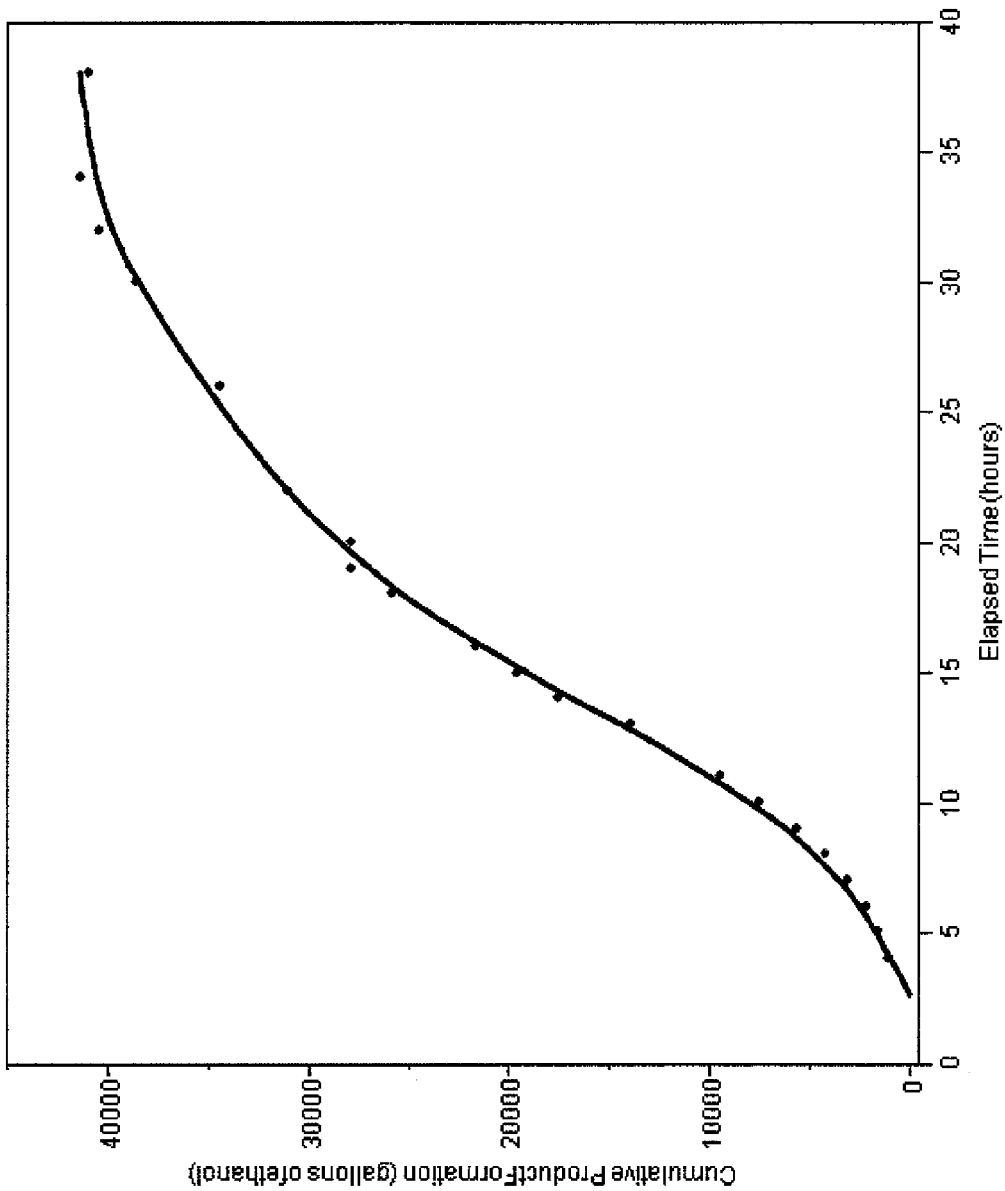
FIG. 7 illustrates fermentation performance that was monitored by tracking cumulative product (ethanol) formation over time where the rate of product formation at any point during batch fermentation can be obtained by the slope of the cumulative product curve.
Figure 8:
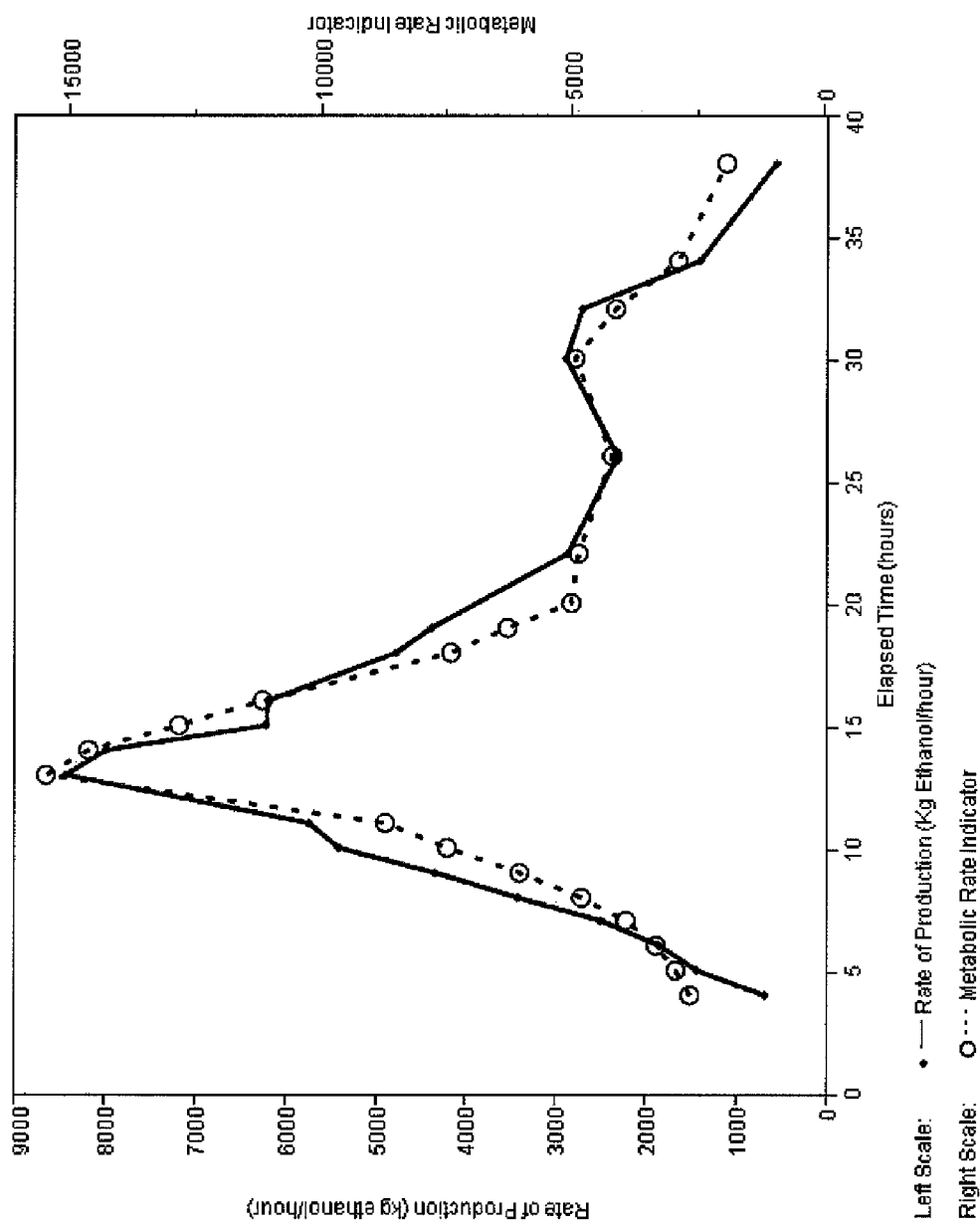
FIG. 8 illustrates an embodiment of the invention where the metabolic rate indicator and the rate of ethanol production are strongly correlated.

In this example, it is demonstrated that the metabolic rate indicator of the instant invention correlates with the rate of ethanol formation during batch fermentation. An industrial batch fermentation of liquefied corn mash was performed with newly propagated yeast. Fermentation performance was monitored by tracking cumulative product formation over time through intermittent high performance liquid chromatography analysis (FIG. 7). The rate of product formation at any point during batch fermentation can be obtained by the slope of the cumulative product curve. As shown in FIG. 8, the rate of ethanol formation and the metabolic rate indicator of the instant invention using the bioreporter O-acetylfluorescein and a pH 7.6 buffer will show a strong correlation.

Example 4

Metabolic Rate Decay of a Cellular Population During Storage

Figure 9:
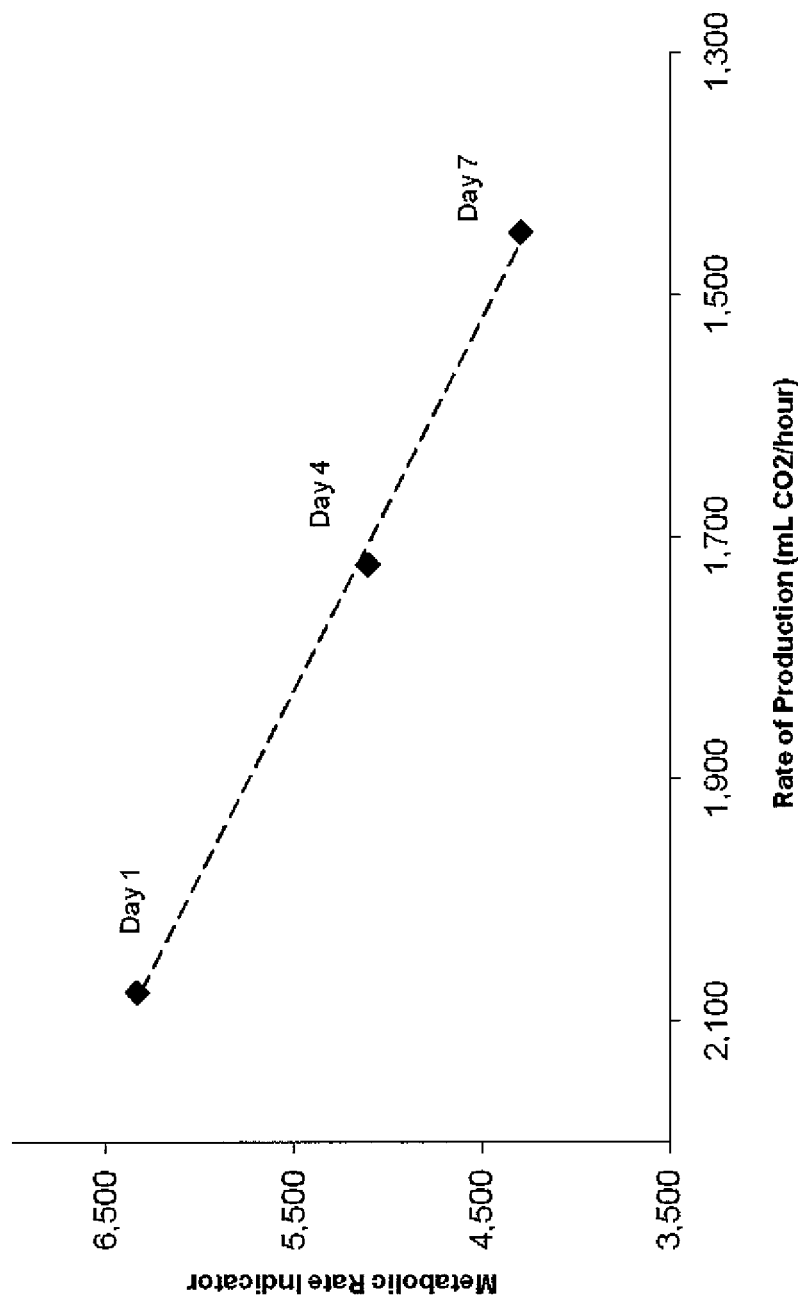
FIG. 9 illustrates an embodiment of the invention where the metabolic rate indicator consistently predicted the decay in metabolic rate during cold storage of a cellular population.

In some circumstances, cellular populations are added directly into a fermentation vessel from a storage environment. This practice is common in the brewing and baking industries, as well as in some fuel ethanol processes where cell recycling occurs. This situation also occurs when the propagation step is skipped and cells in dry form are pitched directly into a fermentation vessel. Under all of these circumstances, it is desirable to know how much cell matter to add. This example demonstrates that the method of the instant invention can be used to predict decaying metabolic rates of a stored population of the bacterium *xanthamonas campestris* using the bioreporter 6,8-difluoro-4-methylumbelliferyl butyrate and pH 7.6 buffer (FIG. 9). This information can be used to determine the amount of cells to add into the next batch rather than adding based on the amount of solids or on the amount of viable cells.

Example 5

Temperature Normalized Metabolic Rates

Figure 10:
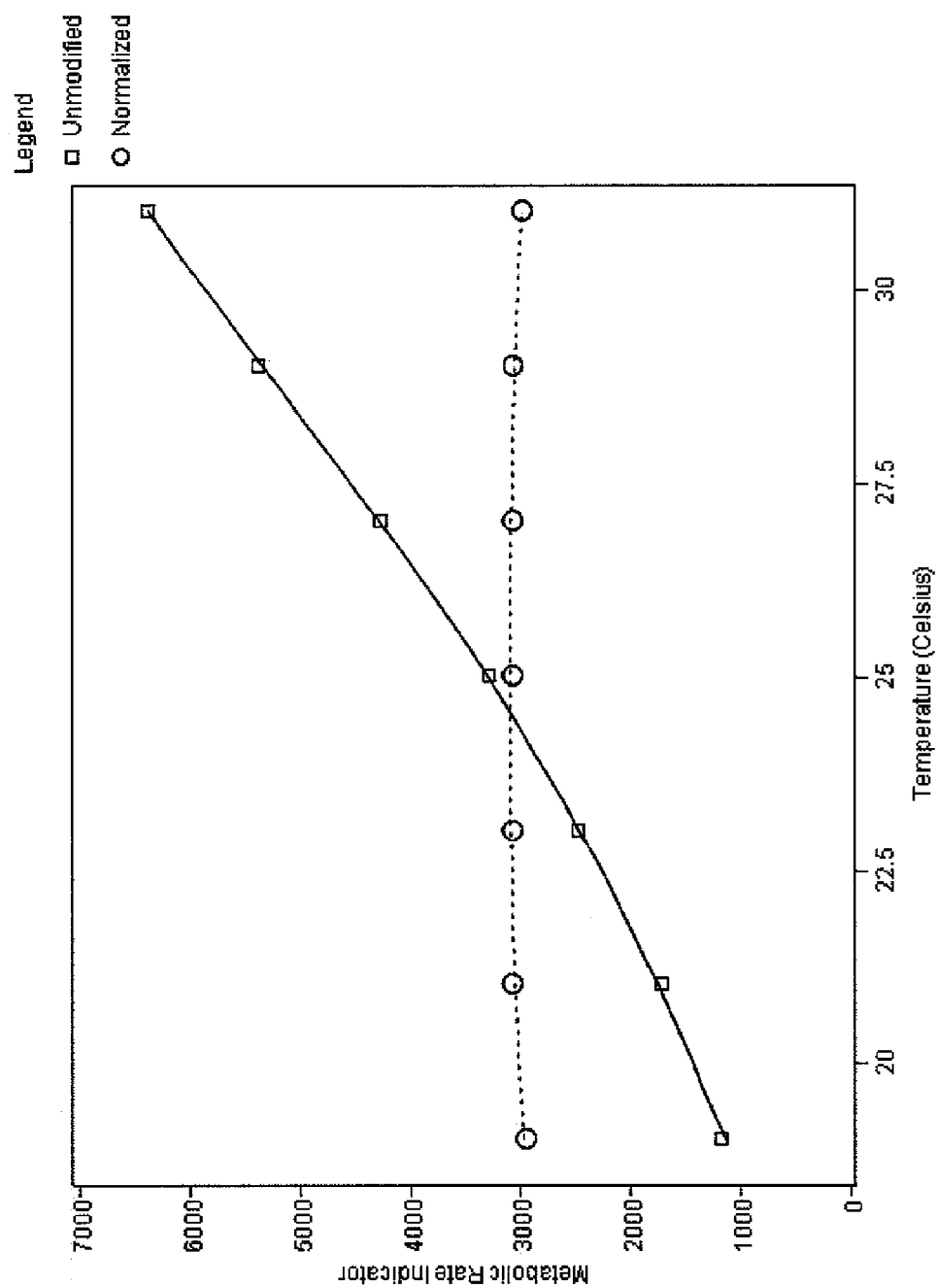
FIG. 10 shows the effect of using a temperature correction algorithm to effectively correct metabolic rates.

This example demonstrates that the method and system of the instant invention can be used to effectively normalize metabolic rates measured at different temperatures for a cellular population of algae measured over the range of normal room temperatures using the bioreporter resorufin acetate and a pH 8.7 buffer (FIG. 10).

Example 6

Turbidity Corrected Metabolic Rates

Figure 11:
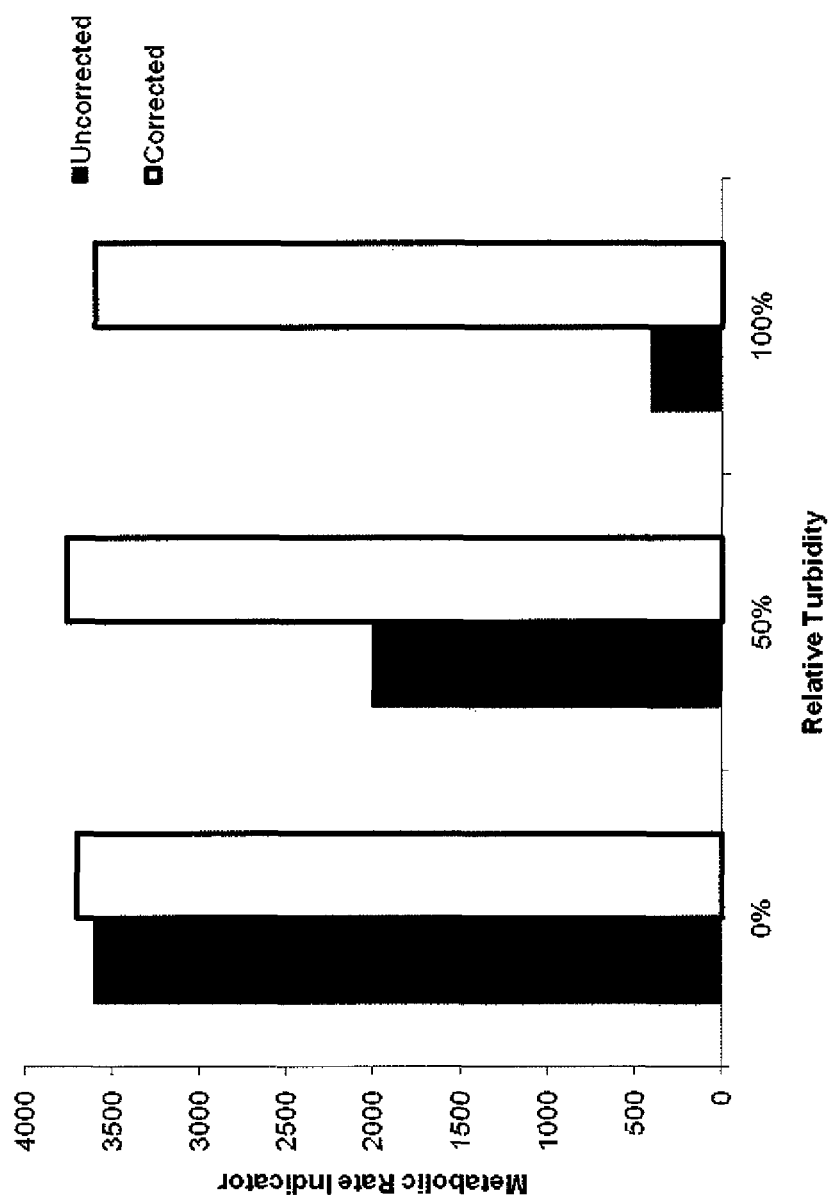
FIG. 11 illustrates improvements for turbidity-corrected metabolic rate determinations as compared to metabolic rates determined from metabolic signals that had not been corrected for the influence of turbidity.

This example demonstrates effective turbidity corrected metabolic rates with the method and system of the instant invention. Metabolic rates for a cellular population of yeast were measured with the method and system of the invention using the bioreporter di-O-acetylfluorescein and a pH 7.6 buffer in the presence of increasing amounts of turbidity contributed by the non-cellular matter in a solution of spent sugar cane extract (FIG. 11). A first set of measurements were made in reference to a calibration model that was constructed in the absence of any non-cellular turbidity (uncorrected data). A second set of metabolic rate determinations were made from the same samples but in reference to the appropriate calibration models constructed in the presence of 0%, 50%, or 100% relative sample turbidity.

All of the compositions and methods disclosed and claimed herein can be made and executed without undue experimentation in light of the present disclosure. While this invention may be embodied in many different forms, there are described in detail herein specific preferred embodiments of the invention. The present disclosure is an exemplification of the principles of the invention and is not intended to limit the invention to the particular embodiments illustrated.

Any ranges given either in absolute terms or in approximate terms are intended to encompass both, and any definitions used herein are intended to be clarifying and not limiting. Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges (including all fractional and whole values) subsumed therein.

Furthermore, the invention encompasses any and all possible combinations of some or all of the various embodiments described herein. Any and all patents, patent applications, scientific papers, and other references cited in this application, as well as any references cited therein, are hereby incorporated by reference in their entirety. It should also be understood that various changes and modifications to the presently preferred embodiments described herein will be apparent to those skilled in the art. Such changes and modifications can be made without departing from the spirit and scope of the invention and without diminishing its intended advantages. It is therefore intended that such changes and modifications be covered by the appended claims.

The claimed invention is:

1. A method of determining a metabolic rate indicator of a cellular population, the method comprising:
   combining a sample containing a cellular population and a bioreporter selected from di-O-propionylfluorescein, di-O-acetylfluorescein, O-acetylfluorescein, 6,8-difluoro-4-methylumbelliferyl butyrate, and resorufin acetate, and optionally an additive, in a vessel equipped with a parameter-detecting device for detecting a parameter, the parameter comprising weight of the sample, volume of the sample, or a combination thereof, wherein combining the sample with the bioreporter and/or the optional additive causes a change in the detected parameter and constitutes an initial point of reaction;
   detecting temperature, turbidity, and metabolic signal of the sample at the initial point of reaction, wherein the metabolic signal correlates to conversion of the bioreporter by the cellular population to a molecule capable of generating a detectable fluorescent signal;
   detecting the temperature, the turbidity, and the metabolic signal of the sample at one or more points in time after the initial point of reaction;
   normalizing the detected metabolic signals for differences in detected temperature by using a temperature normalization algorithm and detected turbidity by calibrating against a mixture of the sample and a standard solution at the initial point of reaction and the one or more points in tune after the initial point of reaction, thereby providing a normalized metabolic signal for the initial point of reaction and for each of the one or more points in time; and
   determining the metabolic rate indicator of the sample based upon the normalized metabolic signals, wherein rate of conversion of the bioreporter by the cellular population to the molecule capable of generating the detectable fluorescent signal correlates with rate of carbon dioxide production or rate of ethanol production by the cellular population.

2. The method of claim 1, wherein the cellular population is selected from bacteria, archae, protists, microscopic animals, fungi, yeast, microscopic plants, animal cells, and any combination of the foregoing.

3. The method of claim 1, wherein the sample of the cellular population is obtained via a manually operated sampler.

4. The method of claim 1, wherein the sample containing the cellular population undergoes separation and resuspension.

5. The method of claim 1, wherein the method is carried out via a vessel comprising the cellular population, a sample collection port, a sample line, and a joint between the sample collection port and the sample line, wherein the joint includes a means to create a fluid communication channel between the sample collection port and the sample line so as to allow a sample of the cellular population to be drawn into the sample line, wherein the sample collection port is in communication with the vessel, wherein the sample line is in communication with the vessel via a valve.

6. The method of claim 5, wherein the metabolic signal is detected via a fluorometer located at least partially inside the vessel.

7. The method of claim 1, further comprising combining additive with the sample containing the cellular population, the bioreporter, and/or combination thereof, wherein the additive causes the parameter to change when combined with the sample, the bioreporter, and/or combination thereof, thereby constituting the initial point of reaction.

8. The method of claim 7, wherein the additive is selected from a buffering agent, a pH modifying agent, a catalyst, a coenzyme, a mineral, a co-substrate, and combinations thereof.

9. The method of claim 7, wherein the additive is a buffering agent that buffers the sample to a pH of approximately 7.6.

10. The method of claim 1, wherein the sample of the cellular population is obtained via an automatically operated sampler.

11. The method of claim 1, wherein the sample of the cellular population is obtained via a sidestream apparatus.

12. The method of claim 1, wherein the sample containing the cellular population is diluted.

\* \* \* \* \*